(12) United States Patent
Fini et al.

(10) Patent No.: US 10,226,565 B2
(45) Date of Patent: Mar. 12, 2019

(54) TUBE FOR EXTRA-CORPOREAL CIRCUIT WITH DOUBLE CONNECTOR

(71) Applicant: Fresenius Medical Care Deutschland GmbH, Bad Homburg (DE)

(72) Inventors: Massimo Fini, Mirandola (IT); Reinhold Reiter, Crema (IT); Wolfgang Wehmeyer, Tuebingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 615 days.

(21) Appl. No.: 14/769,897

(22) PCT Filed: Mar. 18, 2014

(86) PCT No.: PCT/EP2014/055392
§ 371 (c)(1),
(2) Date: Aug. 24, 2015

(87) PCT Pub. No.: WO2014/147061
PCT Pub. Date: Sep. 25, 2014

(65) Prior Publication Data
US 2016/0000988 A1    Jan. 7, 2016

(30) Foreign Application Priority Data

Mar. 20, 2013  (EP) .................................. 13160216

(51) Int. Cl.
*A61M 1/36* (2006.01)
*A61M 39/10* (2006.01)
(Continued)

(52) U.S. Cl.
CPC ............ *A61M 1/367* (2013.01); *A61M 39/10* (2013.01); *A61M 39/12* (2013.01);
(Continued)

(58) Field of Classification Search
CPC .... A61M 1/367; A61M 1/3621; A61M 39/10; A61M 5/14232; A61M 2039/1072;
(Continued)

(56) References Cited

U.S. PATENT DOCUMENTS 5,533,877 A * 7/1996 Friedmann .......... F04B 43/0072
417/477.1
5,661,245 A * 8/1997 Svoboda ........... A61M 5/16854
73/726
(Continued)

FOREIGN PATENT DOCUMENTS

EP        2383004      11/2011
WO     WO 01/32256      5/2001
(Continued)

OTHER PUBLICATIONS 6.1 Notes, Nov. 18, 2008, https://www.fremont.k12.ca.us/cms/lib/CA01000848/Centricity/Domain/2989/Chapter_6_notes.pdf.*

*Primary Examiner* — Bradley J Osinski
*Assistant Examiner* — Nilay J Shah
(74) *Attorney, Agent, or Firm* — Jacobson Holman, PLLC.

(57) ABSTRACT

The present invention relates to a double connector for a tubular insert intended to connect an extra-corporeal circuit to a peristaltic pump. The double connector comprises: a first channel with an axis $a_1$, a second channel with an axis $a_2$ not parallel to $a_1$, a pressure chamber arranged along the first channel and suitable for co-operation with a pressure sensor. The pressure chamber is closed, on the opposite side with respect to the second channel, by a membrane which extends mainly in a plane π substantially parallel to both the axes $a_1$ and $a_2$.
Moreover, a straight line r, passing through both axes $a_1$ and $a_2$ and perpendicular thereto, crosses the membrane. The
(Continued)

invention also relates to a tubular insert comprising the double connector and an extra-corporeal circuit comprising the tubular insert.

9 Claims, 12 Drawing Sheets

(51) Int. Cl.
*A61M 39/12* (2006.01)
*F16L 25/00* (2006.01)
*F16L 37/00* (2006.01)
*F04B 43/00* (2006.01)
*A61M 5/142* (2006.01)

(52) U.S. Cl.
CPC ......... *F16L 25/0018* (2013.01); *F16L 37/008* (2013.01); *A61M 5/14232* (2013.01); *A61M 2039/1072* (2013.01); *A61M 2039/1077* (2013.01); *F04B 43/0072* (2013.01)

(58) Field of Classification Search
CPC ............... A61M 1/3639; A61M 1/1039; F04B 43/0072; F04B 43/12
See application file for complete search history.

(56) References Cited

U.S. PATENT DOCUMENTS

| | | | |
|---|---|---|---|
| 7,603,907 B2 | 10/2009 | Reiter et al. | |
| 2007/0179422 A1* | 8/2007 | Schnell | A61M 1/3639 604/4.01 |
| 2007/0286756 A1* | 12/2007 | Jones | F04B 43/1253 417/477.9 |
| 2013/0030348 A1* | 1/2013 | Lauer | A61M 5/1407 604/6.16 |

FOREIGN PATENT DOCUMENTS

| | | |
|---|---|---|
| WO | WO 2011/134859 | 11/2001 |
| WO | WO 2005/111424 | 11/2005 |
| WO | WO 2007/056363 | 5/2007 |
| WO | WO 2012/143432 | 10/2012 |

\* cited by examiner

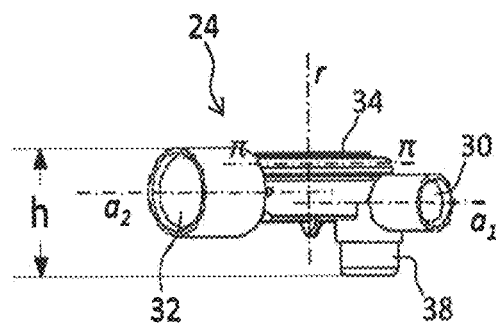
Fig. 16.a
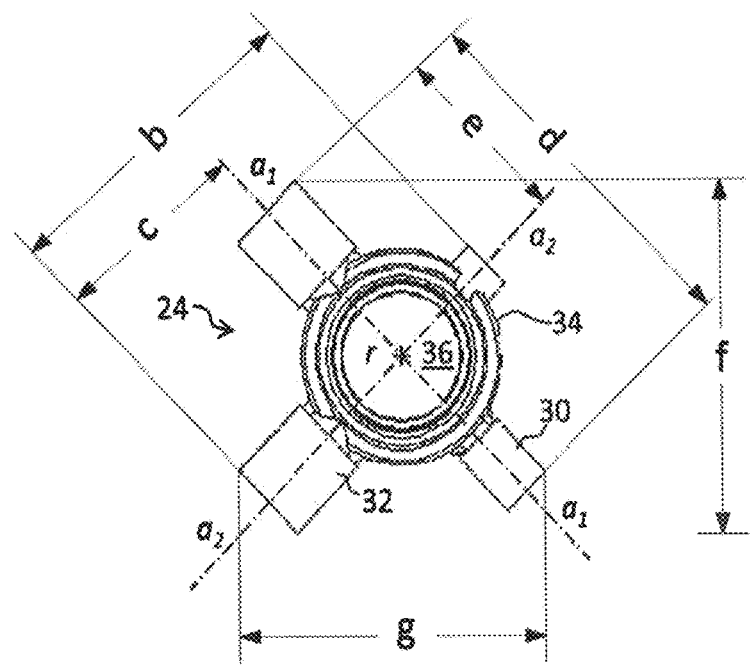
Fig. 16.b

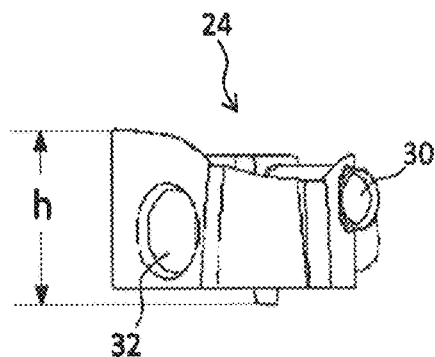
Fig. 17.a  Prior Art
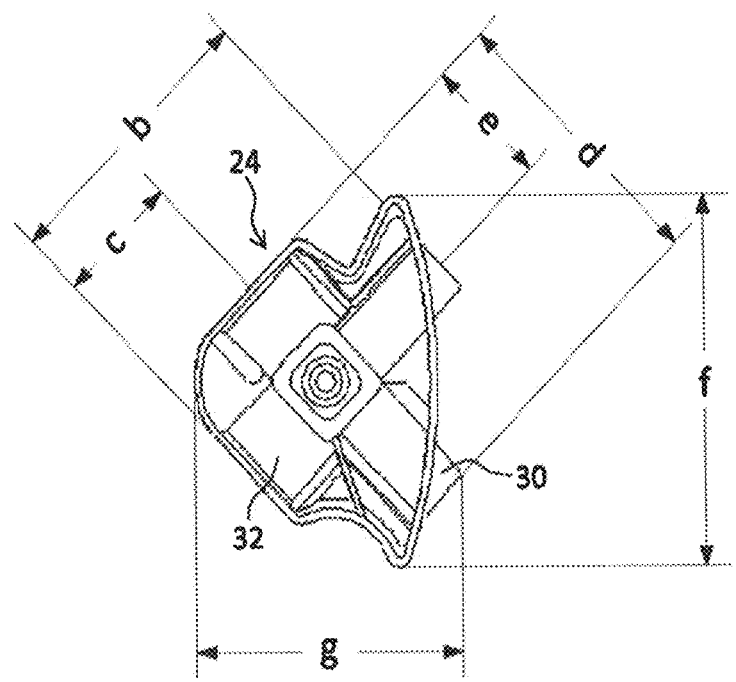
Fig. 17.b  Prior Art

TUBE FOR EXTRA-CORPOREAL CIRCUIT WITH DOUBLE CONNECTOR

The invention relates to a circuit for extra-corporeal circulation and in particular to the tubular insert intended to co-operate with a peristaltic pump and the double connector included in the tubular insert.

In therapeutic treatments which require the use of an extra-corporeal circuit, for example during treatments of haemodialysis, haemofiltration and the like, it is required to ensure circulation of the blood and/or other physiological fluids along the pipes forming the circuit. In this connection it is also required to control the pressure inside the extra-corporeal circuit in order to be able to monitor the correct progress of the therapeutic treatment. In particular situations, the possibility could also be required of supplying or collecting fluids entering or leaving the circuit, for example using syringes or other containers such as bags, bottles, phials and the like.

Obviously the machine which is intended to complete the therapeutic treatment as well as all of its components (for example the peristaltic pump and the pressure sensor) are intended to be used repeatedly with different patients. On the other hand, the extra-corporeal circulation takes place within a disposable circuit.

In order to ensure the circulation inside the extra-corporeal circuit it is known to use peristaltic pumps comprising a stator and a rotor between which a flexible tube is inserted. The rotor of the pump comprises rollers, usually two rollers, suitable for pressing the flexible tube against the stator. The combined action of the pressure exerted by the rollers and the rotation imparted by the rotor causes displacement of the liquid between the two rollers inside the tube. The subsequent and constant displacement of portions of liquid produces in a known manner pumping of the liquid along the circuit.

In order to control the pressure inside the extra-corporeal circuit, the machine which performs the therapeutic treatment usually comprises special sensors.

Finally, in order to be able to supply or collect fluids to/from the circuit, depending on the volume of the fluid, syringes, bags, bottles or the like may be used.

Owing to the requirements mentioned above, it is known to provide each circuit for the extra-corporeal circulation with a tubular insert intended to co-operate with the peristaltic pump, a pressure chamber suitable for co-operating with the pressure sensor and a series of so-called ports which allow the connection of other containers or the safe piercing by means of a syringe needle.

A particularly effective tubular insert has been developed by the Applicant and is widely used in order to facilitate connection of the tube to the peristaltic pump, for example at the time of preparation of the machine for a haemodialysis treatment. Such a tubular insert is described, for example, in the international patent application filed by the same Applicant and published under number WO 2005/111424.

The insert comprises a double connector and a loop formed with a tube section of suitable length and is commonly called an "α insert" owing to its shape. As can be seen in the accompanying FIGS. 2 to 4, this type of insert has overall an α shape since the inlet portion and the outlet portion of the double connector overlap each other. For greater clarity, "inlet portion" is understood as meaning the portion which is intended to be connected to the circuit section coming from the patient, while "output portion" is understood as meaning the portion which is intended to be connected to the circuit section directed towards the machine, for example towards the dialysis filter. As can be noted from the accompanying figures, the inlet portion and the outlet portion intersect, in different planes, inside the double connector.

The loop of the α insert, as can be seen in the accompanying figures, comprises a wide curve which extends along a cylindrical helix which defines an axis intended, during use, to coincide with the axis of rotation of the peristaltic pump. Since the cylindrical helix has a pitch which is decidedly smaller than the curve, by way of a first approximation, it may be considered that the curve lies in a plane and therefore describes an arc of a circumference.

The approximation of the cylindrical helix section with an arc of a circumference having the same diameter D is furthermore justified by the fact that the peristaltic pump acts on the tubular insert exactly as though the latter were extending in a plane perpendicular to the axis X of the rotor. Generally it is considered that this slight geometric discrepancy is adequately compensated for in reality by the deformability of the tube.

The pressure chamber, also known as "pressure dome", is instead designed to create an interface between the circuit and the pressure sensor present on the treatment machine. Obviously it is necessary to prevent the fluids contained in the circuit from contaminating the sensor which is intended to be used repeatedly. On the other hand, the pressure chamber, as well as the entire circuit of which it forms part, are disposable articles. The pressure chamber usually comprises a housing with an inlet connector and outlet connector respectively connected to the circuit. Finally, an elastomeric membrane closes one side of the chamber and is shaped so as to be able to come into contact with the pressure sensor. The elastomeric membrane has a considerable degree of elasticity which allows it to transmit to the sensor the pressure present inside the circuit and the associated variations. A pressure chamber of this type is described in more detail in the US patent granted to the same Applicant under number U.S. Pat. No. 7,603,907.

The pressure chamber, which is situated along a tube of the circuit, must be fixed to the machine so that the membrane rests firmly on the pressure sensor. Generally the pressure chamber is fixed in position by means of a snap-engaging lever which ensures stable positioning during the entire treatment.

A circuit such as that described above, although well established, is not without drawbacks.

For example, the α insert is retained inside the machine by means of a snap-engagement connection provided between the double connector and the respective seat formed in the machine. Obviously, the snap-engagement connection must have a sufficiently easy action to allow any member of staff to easily insert the double connector inside the corresponding seat so as to be able to prepare the machine fir therapeutic treatment. This operation is usually performed with the circuit at room temperature (generally ranging between 20° and 25° C.), while during operation of the machine the circuit heats up until it reaches, in its operating steady condition, a temperature close to body temperature (and therefore in the region of 37° C.). This difference in temperature results in a difference in the mechanical characteristics of the thermoplastic polymer which forms the double connector, in particular heating of the polymer results in a reduction in the rigidity thereof. The interference produced by an easy snap-engaging action at room temperature may therefore be insufficient to hold the connector firmly in position at body temperature.

Moreover, as already mentioned above, the peristaltic pump acts on the α insert as though the loop of the latter were describing an arc of a circumference rather than a section of a cylindrical helix. This approximation is more than valid for the purposes of circulation within the circuit, but is less so from the point of view of the stresses which the rotor rollers impart to the α insert. Owing to the fact that the tube describes in reality a section of a cylindrical helix and the fact that the peristaltic pump acts thereon as though it were flat, the forces generated by the rotor rollers contain components parallel to the axis X of rotation instead of being completely contained within the plane perpendicular thereto. More specifically, a rotation of the pump rotor generates periodic stresses on the α insert which tend to move it in the direction of X and therefore causes the double connector to come out of its seat. This effect, which is negligible in the cold state, may become extremely problematic when the double connector loses its rigidity owing to the operating temperature.

In addition to the drawbacks mentioned above in connection with the α insert of the known type and the double connector in particular, conventional disposable circuits also have another type of drawback. As it will be clear to the person skilled in the art, the double connector, the pressure chamber, as well as the ports, if any, for supplying/removing liquid into/from the channel, need to be connected one another by means of tube portions, so as to become part of the same duct of the extra-corporeal circuit. Such a structure implies some complications during the manufacturing and sterilization steps of the extra-corporeal circuit. Furthermore, the presence of these connection tubes determines for the overall extra-corporeal circuit a length development greater than the strictly necessary one. In turn, a greater length of the circuit implies some negative consequences.

A first negative consequence is that of increasing the time and the volumes of liquid required for the so-called priming, i.e. the operation of filling the circuit with liquid (whether it be blood, physiological solution, replacement liquid, or the like) so as to expel the air or other foreign fluids and make the machine operative.

Another negative consequence of long circuits is that a larger amount of material is required for manufacture thereof. This could seem a negligible aspect but, according to a careful evaluation, it actually appears like a considerable one. The case of haemodialysis is here considered as an example. Since the entire circuit is disposable, it is disposed of after only a single treatment. It is to be considered that, according to a paper published by Michael J. Lysaght, in 2002 the worldwide dialysis population already exceeded one million and had a growth rate of 7% per year. According to some projections, the dialysis patients would have doubled within 2010. Each one of these patients may need three or four treatments per week. Thus it will be clear for the skilled person that the overall amount of material used in the single circuit is not an insignificant item when assessing the sustainability over a long period of time of haemodialysis, both in terms of the environmental impact and in terms of cost for the sanitary services.

The object of the present invention is therefore to solve at least partially the problems mentioned in connection with the circuits for extra-corporeal circulation, and in particular in connection with the tubular inserts, of the known type.

A task of the present invention is to provide a double connector and a tubular insert for extra-corporeal circuits which ensures stable positioning inside the peristaltic pump.

Moreover, a task of the present invention is to provide a double connector and a tubular insert for extra-corporeal circuits which is able to reduce the overall dimensions of the extra-corporeal circuit of which it forms part.

Finally, a task of the present invention is to provide a tubular insert and associated extra-corporeal circuit which have a low-cost.

The abovementioned object and tasks are achieved by a double connector according to the description, by a tubular insert for extra-corporeal circuits according to the description and by an extra-corporeal circuit according to the description.

The characteristic features and further advantages of the invention will emerge from the description provided hereinbelow, of a number of examples of embodiment, provided by way of a non-limiting example, with reference to the accompanying drawings in which.

Figure 1:
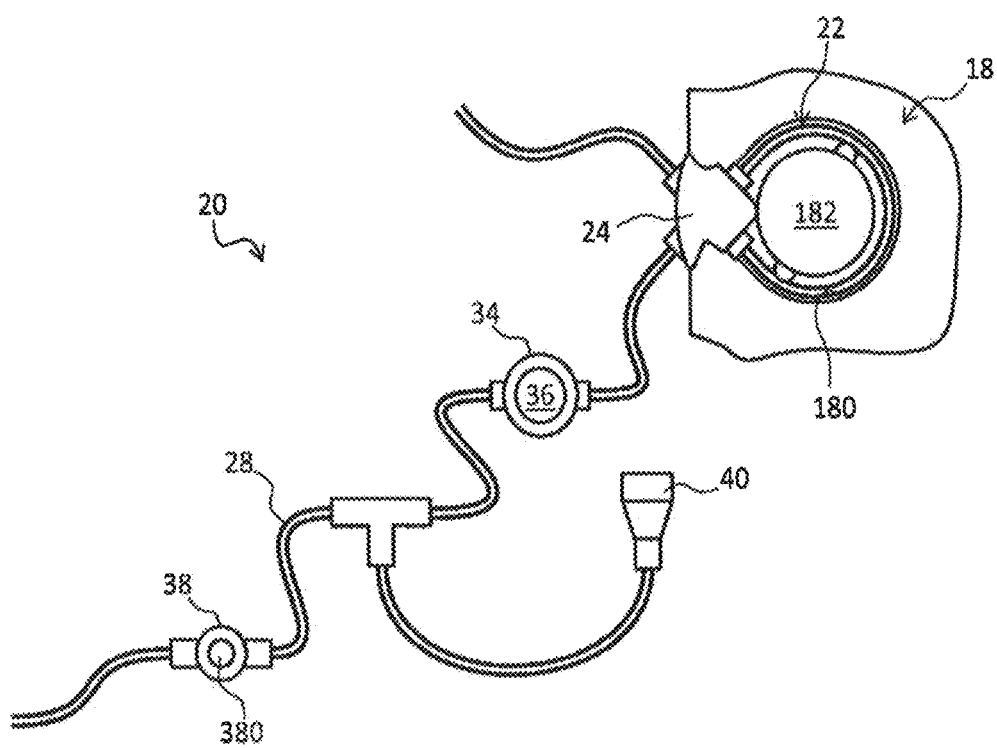
FIG. 1 shows in schematic form an extra-corporeal circuit according to the prior art used in haemodialysis treatment.
Figure 2:
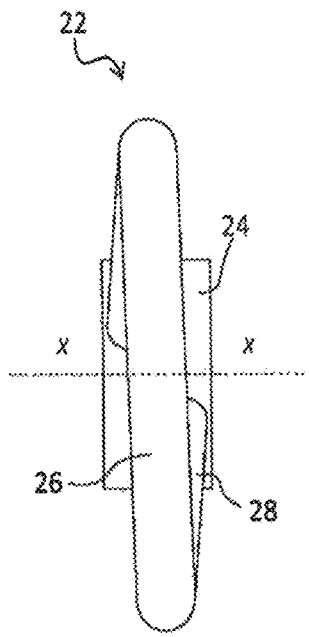
FIG. 2 shows schematically a first view of an α insert of the known type used in a circuit similar to that of FIG. 1.
Figure 3:
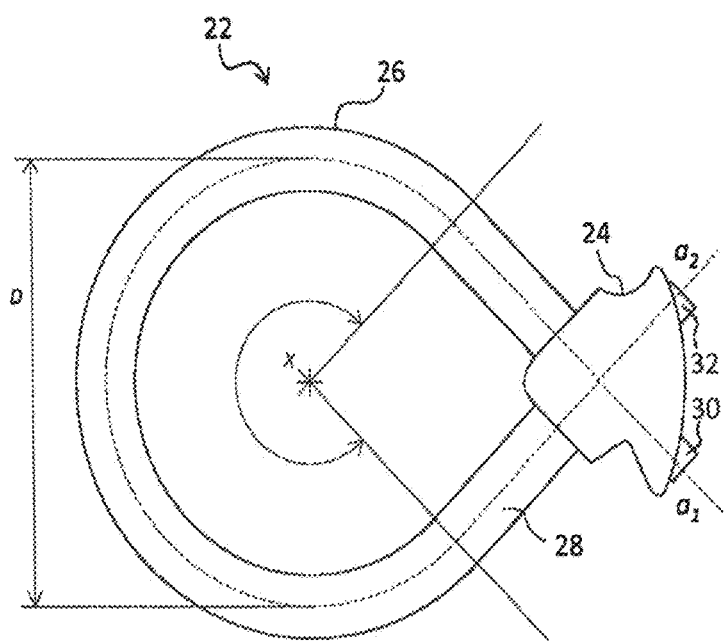
FIG. 3 shows schematically a second view of the α insert according to FIG. 2.
Figure 4:
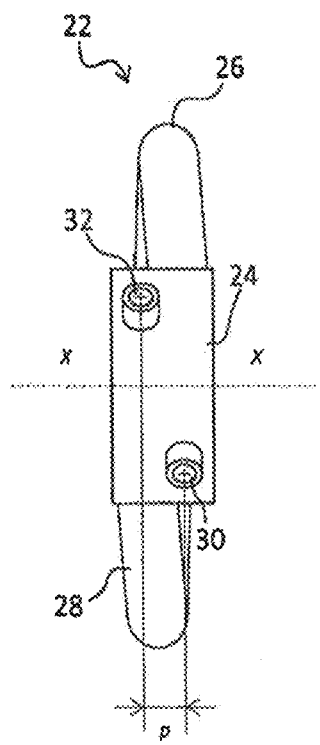
FIG. 4 shows schematically a third view of the α insert according to FIG. 2.
Figure 5:
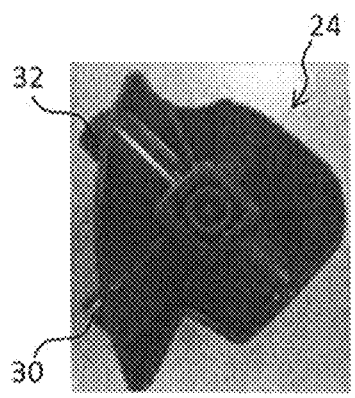
FIG. 5 shows schematically a double connector used in an α insert of the known type used in a circuit similar to that of FIG. 1.
Figure 6:
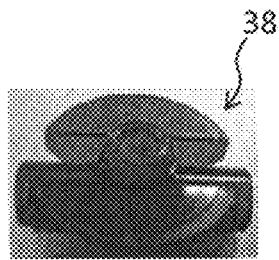
FIG. 6 shows a port of the known type suitable for being pierced by the needle of a syringe and used in a circuit similar to that of FIG. 1.
Figure 7:
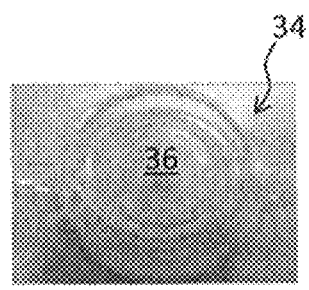
FIG. 7 shows a pressure chamber of the known type used in a circuit similar to that of FIG. 1.

FIGS. 16.a and 16.b show two views of an embodiment of the double connector according to the invention, with a number of significant dimensions; and FIGS. 17.a and 17.b show two views, similar to those of FIGS. 16.a and 16.b, of an embodiment of the double connector according to the prior art, with a number of significant dimensions.

In the description below, the reference number 20 denotes in its entirety an extra-corporeal circuit of the type commonly used in treatments which require an extra-corporeal circulation, such as haemodialysis, haemofiltration and the like.

The extra-corporeal circuit 20 comprises a tubular insert 22 intended to connect the extra-corporeal circuit 20 to a peristaltic pump 18. The tubular insert 22 comprises a double connector 24 and a loop 26 formed by a tube section 28 of suitable length.

According to a first aspect of the present invention, the double connector 24 comprises:
a first channel 30 with an axis $a_1$;
a second channel 32 with an axis $a_2$ not parallel to $a_1$;

a pressure chamber 34 arranged along the first channel 30 and suitable for cooperating with a pressure sensor 16, the pressure chamber being closed, on the opposite side with respect to the second channel 32, by a membrane 36 which extends mainly in a plane π substantially parallel to both the axes $a_1$ and $a_2$.

In the double connector 24 according to the invention, a straight line r passing through both the axes $a_1$ and $a_2$ and perpendicular thereto, crosses the membrane 36.

According to an embodiment, the double connector 24 also comprises a piercible insert 38 arranged along one of the two channels 30 or 32. The insert 38 is of the type which can be pierced by the needle of a syringe, typically in order to supply or remove a liquid into/from the underlying channel 30 or 32. The insert 38 may be arranged along the first channel 30 (as shown in FIGS. 8 to 16), along the second channel (solution not shown) or an insert 38 may be arranged on each of the two channels 30 and 32 (solution not shown).

According to an embodiment, the double connector 24 also comprises a port 40 arranged along one of the two channels 30 or 32. The port 40 is of the type suitable for connection to an external container in order to supply/remove a liquid into/from the channel 30 or 32. The container may be, for example, a bottle, a bag, a phial or the like.

Figure 15:
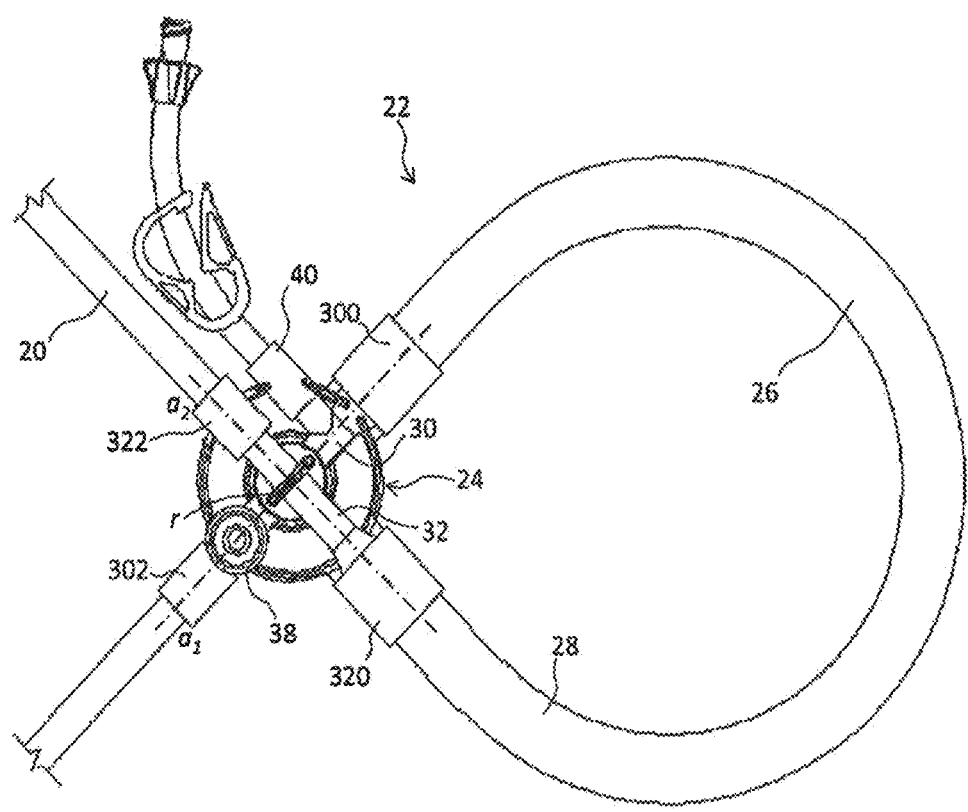
FIG. 15 shows an α insert according to the invention.

The port 40 may be arranged along the first channel 30 (as shown in FIG. 15), along the second channel (solution not shown) or a port 40 may be arranged on each of the two channels 30 and 32 (solution not shown).

As can be clearly understood from the description given above, the double connector 24 according to the invention allows the extra-corporeal circuit 20 to have overall an extremely compact design. In fact, the double connector 24 also comprises the pressure chamber 34, which in the solution according to the prior art, was formed as a separate component arranged along the circuit.

With reference to FIGS. 16 and 17, the main dimensions of the double connector 24 according to the prior art are shown below, compared with the corresponding dimensions of the double connector 24 according to the invention.

| PRIOR ART | | INVENTION | |
|---|---|---|---|
| h | 24.34 | h | 17.27 |
| b | 41.15 | b | 46 |
| c | 18.45 | c | 28 |
| d | 41.15 | d | 54 |
| e | 18.45 | e | 28 |
| f | 51.7 | f | 48.08 |
| g | 40.38 | g | 45.11 |

The compact nature of the double connector 24 according to the invention may be appreciated more fully when one considers the fact that, in the particular embodiments shown in FIG. 16, it encloses within it also the pressure chamber 34 and the piercible insert 38.

Moreover, the double connector 24 according to the invention, comprising the pressure chamber 34, may in turn be kept firmly in position by means of the snap-engaging lever which, in a manner known per se, keeps the pressure chamber 34 pressed against the pressure sensor 16 of the machine. In this way, as will be now clear to the person skilled in the art, most of the problems described in connection with the prior art and associated with coupling of the connector to the respective seat on the machine are solved. In particular, it is no longer required to provide the snap-engagement connection owing to the presence of the snap-engaging lever intended to keep the pressure chamber 34 in position. It should be noted how, owing to the double connector 24 according to the invention, the service personnel does not have to perform any additional operation during preparation of the machine; on the contrary, it is required to fix only one component (the connector comprising the pressure chamber) instead of the two separate components as in the known solution (the connector and the pressure chamber).

It should be noted, moreover, that, as a result of fixing of the double connector 24 by means of the snap-engaging lever, the fixing force remains constant during treatment and in particular is independent of the operating temperature and the mechanical characteristics of the polymer which forms the double connector 24. It should be also noted how, owing to fixing of the double connector 24 by means of the snap-engaging lever, it may be kept firmly in position even though the forces applied by the rotor 182 onto the loop 26 have non-zero components directed along the axis X.

The compactness characteristics of the double connector 24 according to the invention are accentuated even further in the embodiments which also comprise one or more piercible inserts 38 and/or one or more ports 40. These components also, in the solution according to the prior art, were distributed along the extra-corporeal circuit 20, thus making it longer.

In order to appreciate more fully some of the characteristic features of the invention and the advantages resulting therefrom, a double connector according to the prior art will be described in detail below with reference to FIGS. 1 to 4. In order to facilitate understanding, the same reference numbers are used to indicate parts corresponding to each other and/or performing the same functions in the connector according to the prior art and the connector according to the invention.

As can be seen in the accompanying figures, the tubular insert 22 has overall an α shape since, in the double connector 24, the first channel 30 and second channel 32 overlap each other. For greater clarity, with specific reference to FIG. 1, the first channel 30 is the inlet channel, intended to be connected to the circuit section coming from the patient, while the second channel 32 is the outlet channel 36, intended to be connected to the circuit section directed towards the treatment machine, for example towards the dialysis filter. As can be clearly noted from the accompanying FIGS. 2 and 4, the first channel 30 and the second channel 32 intersect, in different planes, inside the double connector 24.

The loop 26, as can be seen in the accompanying figures, comprises a wide curve 24 which extends along a cylindrical helix and is connected to the connector 24 by means of two substantially straight tube segments. The cylindrical helix along which the curve of the loop 26 extends defines an axis intended, during use, to coincide with the rotation axis of the rotor 182 of the peristaltic pump 18. Both these axes are indicated below by a single reference letter X since, during use, they coincide along a single axis. Moreover, the cylindrical helix has a pitch p which is decidedly smaller than the diameter D such that, according to a first approximation, it may be considered that the curve lies in a plane and therefore describes an arc of a circumference. It may be considered, for example, that, according to a first preferred embodiment, the diameter D of the cylindrical helix is about 50 mm, while the pitch p is only about 6 mm.

The approximation of the cylindrical helix section with an arc of a circumference having the same diameter D is furthermore justified in that the peristaltic pump 18 acts on the tubular insert 22 exactly as though the latter were extending in a plane perpendicular to the axis X of the rotor 182. This slight geometric discrepancy is usually assumed to be fully compensated for in reality by the deformability of the tube 78.

The loop 26 is intended to be inserted between the stator 180 and the rotor 182 of the peristaltic pump 18. In the loop 26 of the tubular insert 24, the curve extends preferably along an arc a with an amplitude greater than 180°, so as to be able to co-operate effectively with the rotor 182, the rollers of which are generally two in number and arranged at a distance of 180° from each other. For example, in the embodiment of the tubular insert 22 shown in FIG. 3, the curve extends along an arc which has an amplitude of about 270°. It should be noted here that this configuration will generally be assumed by the loop 26 only when it is inserted inside the peristaltic pump 18, while, during the non-operative phases where the tubular insert 22 is separated from the peristaltic pump 18, the loop 26 will assume a generally different form determined solely by the reactions inside the tube 28.

Figure 13:
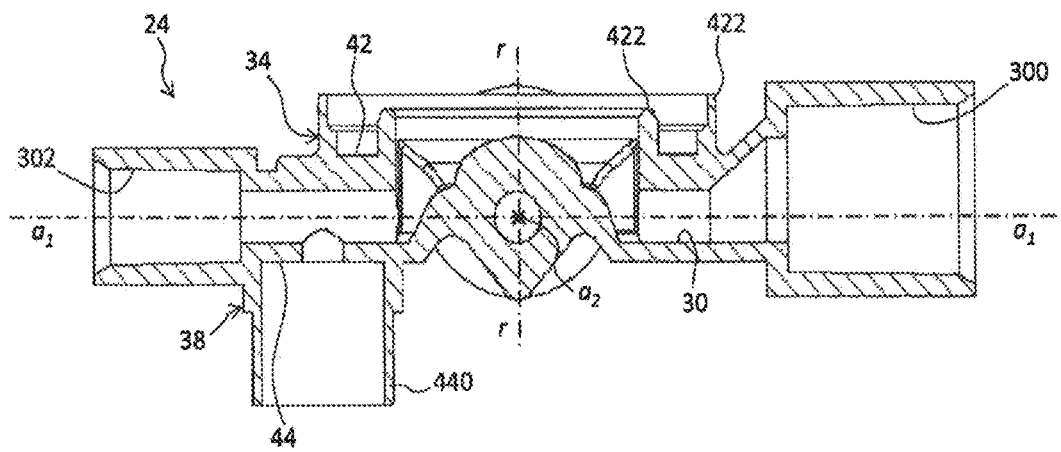
FIG. 13 shows a cross-sectional side view along the axis $a_1$ of FIG. 11.
Figure 14:
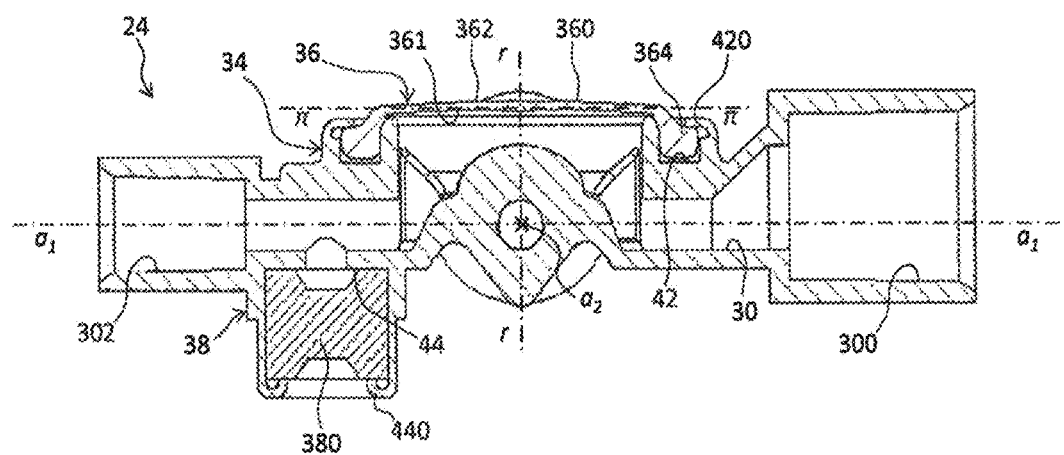
FIG. 14 shows a cross-sectional side view along the axis $a_2$ of FIG. 9.

In accordance with a number of embodiments of the double connector 24 according to the present invention, for example those shown in FIGS. 13 and 14, the axis $a_1$ of the first channel 30 and the axis $a_2$ of the second channel 32 lie in the same plane. In accordance with other embodiments, on the other hand, the two axes $a_1$ and $a_2$ are offset relative to each other (as shown in FIG. 16.*a*). In any case the geometrical definitions given above and relating to the straight line r and to the plane π are nevertheless valid.

The possibility of providing the double connector 24 according to the invention with a coplanar arrangement of the axes $a_1$ and $a_2$ is the result of the integration of the pressure chamber 34 inside the first channel 30. If we consider, for example, the longitudinal section through a pressure chamber of the known type shown in FIG. 8, as can be seen, this pressure chamber 34 has a main axis, indicated here by $a_1$, which is common to the inlet connector and the outlet connector. Despite this, however, the longitudinal profile of the duct defined by the pressure chamber 34 comprises a deviation from the axis $a_1$ towards the membrane 36 and then back to towards the axis $a_1$. This path, which is optimized in order to achieve precise measurement of the pressure by means of the membrane 36, allows the second channel 32 to intersect the first channel 30, while maintaining the respective axes $a_2$ and $a_1$ in the same plane without the need of designedly deviating the flow. It should be noted, in fact, that any deviation of the flow of this type results in a loss of head which reduces the overall efficiency of the extra-corporeal circuit. It is therefore extremely advantageous to make use of the flow deviation already present in the pressure chamber 34 for other reasons.

The fact that the axes $a_1$ and $a_2$ are coplanar has the effect that the loop 26 of the double connector 24 according to the present invention in reality lies in one plane and that it therefore describes an arc of the circumference rather than a cylindrical helix section as was the case for the α insert of the known type.

In the light of all what stated above, the advantages of a double connector 24 according to the present invention will now be quite clear if, in the said connector, the axis $a_1$ of the first channel 30 and the axis $a_2$ of the second channel 32 are coplanar. In fact, such a double connector 24 may solve the abovementioned problems arising from the approximation which occurs in the peristaltic pump 18 with the connectors of the known type. The fact that the loop 26 in reality lies in one plane in fact neutralizes the components along the axis X of the stresses applied by the rollers of the rotor 182 onto the tubular insert 22. The neutralization of these stresses therefore has the effect of making more stable positioning of the insert 22 in the peristaltic pump 18, and in particular positioning of the double connector 24 in its seat on the machine.

Preferably, both the channels 30 and 32 of the double connector 24 comprise an end 300 and 320 suitable for connection to a flexible tube 28 intended to form the loop 26 designed to be seated between the stator 180 and the rotor 182 of the peristaltic pump 18.

According to a second aspect thereof, the present invention relates to the tubular insert 22 intended to connect the extra-corporeal circuit 20 to the peristaltic pump 18. The tubular insert 22 according to the invention comprises a double connector 24 of the type described above and the flexible tube portion 28 which forms the loop 26 is intended to be seated between the stator 180 and the rotor 182 of the peristaltic pump 18.

Preferably, both the channels 30 and 32 of the double connector 24 comprise an end 302 and 322 suitable for connection to a flexible tube 28 intended to form a portion of the extra-corporeal circuit 20. In particular, a first portion of the extra-corporeal circuit 20 is designed to connect the patient to the tubular insert 22, while a second portion of the extra-corporeal circuit 20 is designed to connect the tubular insert 22 to the machine component which performs the treatment, for example the dialysis filter.

According to a third aspect thereof, the present invention relates to the entire extra-corporeal circuit 20 designed to be connected to the peristaltic pump 18. The extra-corporeal circuit 20 according to the invention comprises the tubular insert 22 of the type described above.

The tube 28 of the tubular insert may be made of silicone, plasticized PVC (e.g. plasticized with DOP (dioctyiphtalate) or with TOTM (trioctyl-trimellitate)), PP, or another elastomer suitable for medical use.

According to some embodiments of the double connector according to the invention, the membrane 36 comprises an elastic circular wall 360 and a circular rim 364. The elastic circular wall 360 is designed to close one side of the pressure chamber 34 so as to define a division between the interior of the pressure chamber 34 and the exterior. The circular rim 364 is designed to be connected to the body of the pressure chamber 34.

Moreover, in certain embodiments, the elastic circular wall 360, when there is no difference in the pressures acting on the inner side 361 and on the outer side 362, respectively, has an outwardly convex form.

Here "inner" is understood as meaning the part of the pressure chamber 34 which, during use, is occupied by the physiological liquid. In relation to the membrane 36, therefore, the inner side 361 is that side which, during use, is wetted by the physiological liquid, while the outer side 362 is that side which, during use, comes into contact against the pressure sensor 16 of the machine.

The membrane 36, therefore, in addition to being flat, may also have a double curvature.

In other words, the elastic circular wall 360 may assume the form of a dome, for example a dome forming part of a sphere or a different solid of rotation.

According to some embodiments of the invention, the distance between the outermost point of the dome and the plane π containing the base circumference is between 1% in 2% of the diameter of the base circumference of the dome.

The membrane 36 is preferably made as one piece. In other words, the rim 364 is preferably formed integrally and as one piece with the wall 360. Even more preferably, the rim 364 and the wall 360 are formed by means of injection-moulding of a single material. For example, the membrane 36 may be made, in a manner known per se, of thermoplastic elastomer, silicone or other elastomers suitable for contact with the physiological fluids.

The outwardly convex shape of the membrane 36 eliminates any risk of air bubbles remaining trapped between the membrane itself and the pressure sensor 16 when the double connector 24 is arranged in position. In fact, the contact between the membrane 36 and the pressure sensor 16 occurs gradually, starting from the centre (i.e. from the outermost point of the wall 360) and progressing gradually towards the periphery. In this way, the air is gradually expelled externally.

Moreover, the convex shape of the membrane 36 has the effect that, following relaxation due to ageing of the elastomer or the operating conditions to which the membrane 36 is subject, the wall 360 is able to maintain its functionality. Any relaxation will result in the worst of cases in a reduction in the convexity, but it is unlikely that it will be manage to eliminate it and/or invert, the curvature of the wall 360 until it becomes concave.

A membrane similar to that described above is described in greater detail in the international patent application filed by the same Applicant and published under number WO 2011/134859.

According to some embodiments, the body of the double connector 24 defines a seat 42 for stably housing the membrane 36; the seat is in particular configured to receive the rim 364 of the membrane 36.

The body of the double connector 24 is preferably produced, in a manner known per se, by means of injection-moulding of a polymer which is sufficiently rigid and suitable for contact with the physiological fluids. Polymers which are suitable for this type of use may be for example: polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS) and copolyesters.

Figure 11:
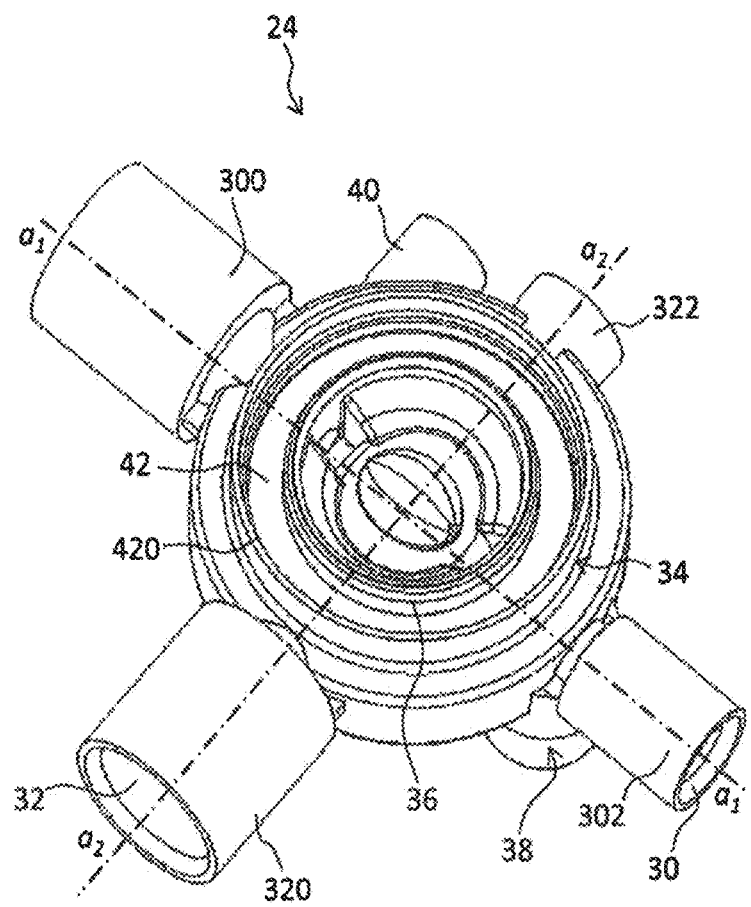
FIG. 11 shows, in a view similar to that of FIG. 9, the main body of a double connector according to the invention.

According to the embodiment shown in FIGS. 11 and 13-14, the seat 42 is defined by an edge 420 and by an inner wall 422. The edge 420 allows the membrane 36 to be fixed inside the seat 42. According to these embodiments, the double connector 24 is preferably produced with the edge 420 formed as a cylindrical wall (see in particular FIGS. 11 and 13). When the membrane 36 is assembled on the double connector 24, so as to form the complete pressure chamber 34, the rim 364 of the membrane 36 is housed inside the corresponding seat 42. Then the edge 420 is folded over so as to press against the rim 364 of the membrane 36 and thus keep it inside the corresponding seat 42 (see in particular FIG. 14).

This system for fixing the membrane 36 obtained by means of deformation of the edge 420 is known as beading. Deformation of the edge 420 may be obtained, in a manner known per se in the sector of polymer processing, by means of heat application, ultrasound or spin welding. Beading is carried out in such a way that the pressure chamber 34 as a whole is hermetically sealed, with the exception, obviously, of the openings which form the inlet and outlet of the first channel 30. In other words, the joint between the membrane 36 and the body of the double connector 24 must prevent the physiological liquid, which is intended to occupy the pressure chamber 34, from infiltrating between the seat 42 and the membrane 36 and therefore from escaping externally.

Figure 8:
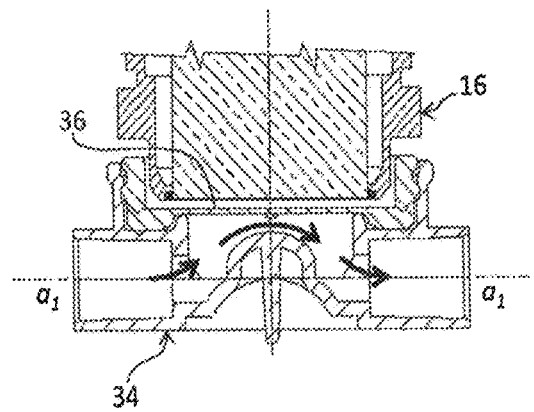
FIG. 8 shows a longitudinal section through a pressure chamber of the known type connected to a pressure sensor.
Figure 9:
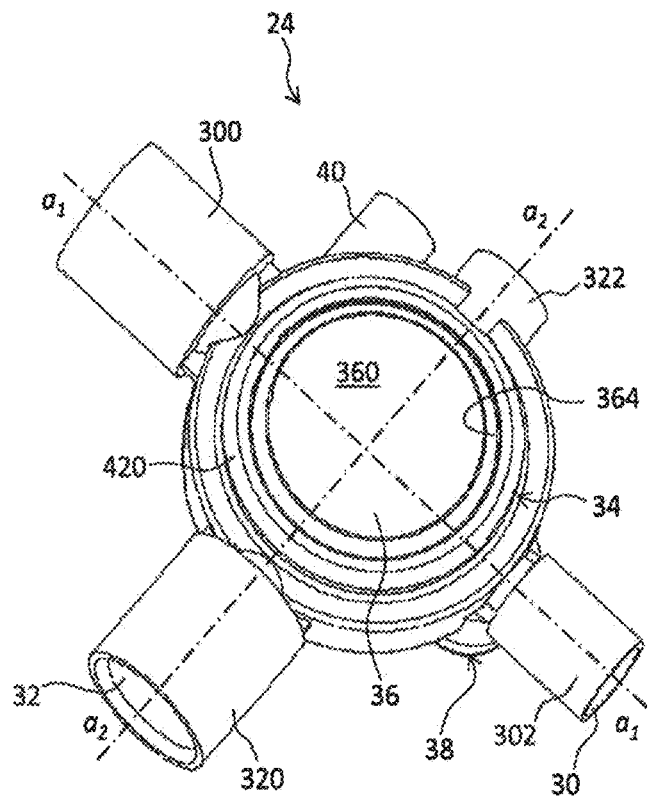
FIG. 9 shows a first view of a double connector according to the invention.
Figure 10:
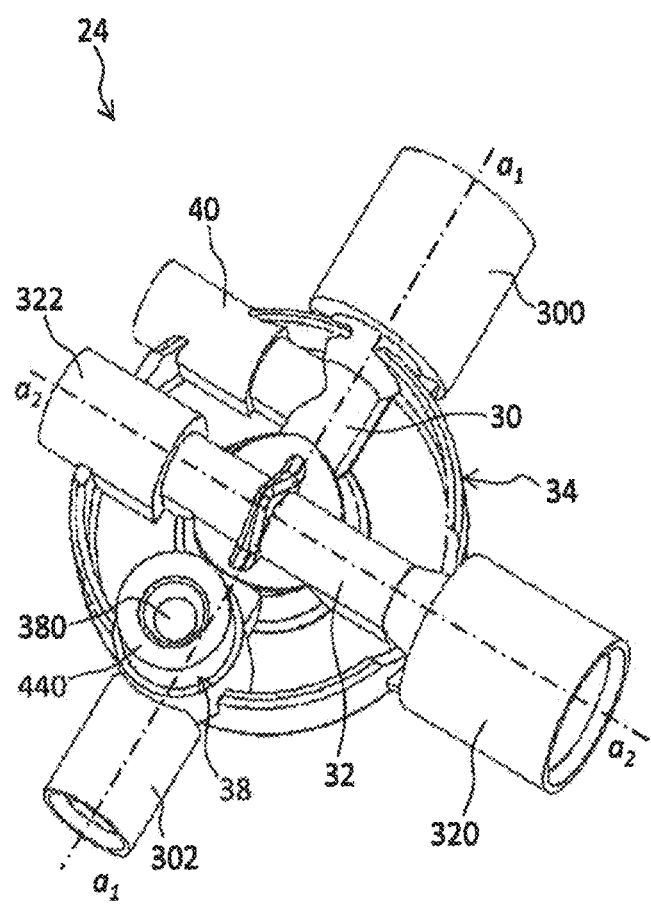
FIG. 10 shows a second view of a double connector according to the invention.

According to other embodiments, not shown, the membrane 36 is fixed to the body of the double connector 24 by means of a rigid ring, in a manner known per se for example by the pressure chamber shown in FIG. 8. The connection between the rigid ring and the body of the double connector 24 may be of the snap-engaging type, screw/female thread type, interference-fit type, or the like.

According to certain embodiments, the membrane 36 and the ring are made separately, while in other embodiments they are made by means of two-component injection moulding. This therefore produces, in a manner known per se, a single part made of two different materials.

Solutions similar to those described above are described in greater detail in the international patent application filed by the same Applicant and published under number WO 2011/134859.

The same comments made above concerning fixing of the membrane 36 to the body of the double connector 24 are applicable also to fixing of the piercible insert 38. In particular, according to some embodiments, the body of the double connector 24 defines a seat 44 for stably housing the plug 380 and thus defining the piercible insert 38.

Figure 12:
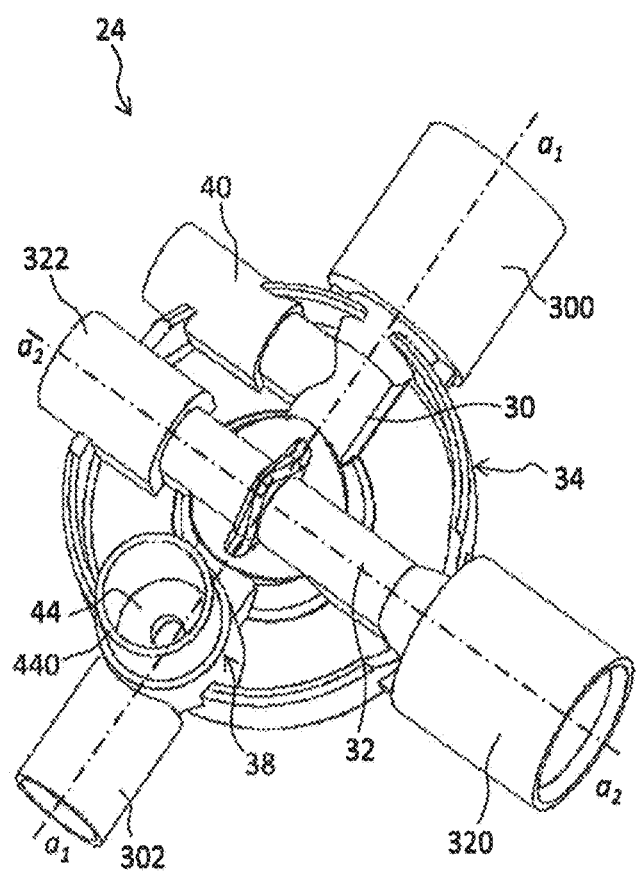
FIG. 12 shows, in a view similar to that of FIG. 10, the main body of a double connector according to the invention.

According to the embodiment shown in FIGS. 12 and 13-14, the seat 44 is defined by an edge 440 which allows the plug 380 to be fixed inside the seat 44. According to these embodiments, the double connector 24 is preferably produced with the edge 440 formed as a cylindrical wall (see in particular FIGS. 12 and 13). When the plug 380 is assembled on the double connector 24, so as to form the complete piercible insert 38, the plug 380 is housed inside the corresponding seat 44. Then the edge 440 is folded over so as to press against the plug 380 and thus keep it inside the corresponding seat 44 (see in particular FIG. 14).

As already mentioned above in connection with the membrane 36, said fixing by means of beading may be obtained, in a manner known per se, by means of heat application, ultrasound or spin welding. Beading is carried out in such a way that the piercible insert 38 as a whole is hermetically sealed, with the exception, obviously, of the opening in the channel. In other words, the joint between the plug 380 and the body of the double connector 24 must prevent the physiological liquid from infiltrating between the seat 44 and the plug 380 and therefore from being able to escape externally.

According to other embodiments, not shown, the plug 380 is fixed to the body of the double connector 24 by means of a rigid ring, in a manner known per se. The connection between the rigid ring and the body of the double connector 24 may be of the snap-engaging type, screw/female thread type, interference-fit type, or the like.

According to certain embodiments, the plug 380 and the ring are made separately, while in other embodiments they are made by means of two-component injection moulding. This therefore produces, in a known manner, a single part made of two different materials.

As the person skilled in the art can certainly understand from that described above, the double connector 24, the tubular insert 22 and the extra-corporeal circuit 20 according to the invention are able to solve at least partially the drawbacks mentioned above in relation to the prior art.

In particular, in addition to the advantages explained in detail above with direct reference to the specific technical characteristics, the double connector and the tubular insert described above are suitable for giving the extra-corporeal circuit a particular compactness. Such compactness allows reducing the costs and the environmental impact of the disposable extra-corporeal circuits. Moreover, the extra-corporeal circuit according to the invention allows easier manufacture and sterilization steps.

With regard to the embodiments of the double connector, the tubular insert and the extra-corporal circuit described above, the person skilled in the art may, in order to satisfy specific requirements, make modifications to and/or replace elements described with equivalent elements, without thereby departing from the scope of the accompanying claims.

The invention claimed is:

1. A double connector for a tubular insert intended to connect an extra-corporeal circuit to a peristaltic pump, the double connector comprising:
   a first channel extending along an axis $a_1$;
   a second channel extending along an axis $a_2$ not parallel to the axis $a_1$;
   a pressure chamber integrated inside the first channel and suitable for co-operating with a pressure sensor, the pressure chamber being closed, on an opposite side with respect to the second channel, by a membrane extending mainly in a plane $\pi$ substantially parallel to both the axes $a_1$ and $a_2$;
   wherein a straight line r, passing through both the axes $a_1$ and $a_2$ and perpendicular thereto, crosses the membrane, and wherein the axis $a_1$ of the first channel and the axis $a_2$ of the second channel are coplanar.

2. The double connector according to claim 1, further comprising a piercible insert arranged along one of the two channels, the insert being piercible with a needle so as to supply or remove a liquid to/from the channel along which the piercible insert is arranged.

3. The double connector according to claim 2, wherein the membrane and/or a plug of the piercible insert are retained inside respective seats by beading of an edge of each respective seat.

4. The double connector according to claim 1, further comprising a port arranged along one of the two channels, the port being suitable for connection to a container so as to supply or remove a liquid to/from the channel along which the port is arranged.

5. The double connector according to claim 1, wherein both the channels comprise one end suitable for connection to a flexible tube intended to form a loop designed to be seated between a stator and a rotor of the peristaltic pump.

6. The double connector according to claim 1, wherein both the channels comprise an end suitable for connection to a flexible tube intended to form a portion of the extra-corporeal circuit.

7. The double connector according to claim 1, wherein the membrane comprises an elastic circular wall having inner and outer sides which, when there is no difference in pressures which act on the inner side and on the outer side, respectively, has an outwardly convex form.

8. A tubular insert intended to connect an extra-corporeal circuit to a peristaltic pump, comprising the double connector according to claim 1 and a tube section which forms a loop intended to be seated between a stator and a rotor of the peristaltic pump.

9. An extra-corporeal circuit designed to be connected to a peristaltic pump, said circuit comprising the tubular insert according to claim 8.

* * * * *